US00PP29223P2

(12) United States Plant Patent
Smith

(10) Patent No.: US PP29,223 P2
(45) Date of Patent: Apr. 10, 2018

(54) ***CHRYSANTHEMUM* PLANT NAMED 'CIFZ0057'**

(50) Latin Name: *Chrysanthemum×morifolium*
Varietal Denomination: CIFZ0057

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/530,553

(22) Filed: Jan. 27, 2017

(51) Int. Cl.
*A01H 5/02* (2006.01)

(52) U.S. Cl.
USPC ..... Plt./290

(58) Field of Classification Search
USPC ..... Plt./290
CPC ..... A01H 5/0255
See application file for complete search history.

*Primary Examiner* — Kent L Bell
(74) *Attorney, Agent, or Firm* — Dale Skalla

(57) ABSTRACT

A new garden type *Chrysanthemum* plant named 'CIFZ0057' particularly distinguished by the medium sized (1.75+ inch) orange decorative flowers, compact sized plant with round mound habit and a natural season response in early September.

1 Drawing Sheet

Figure 1:
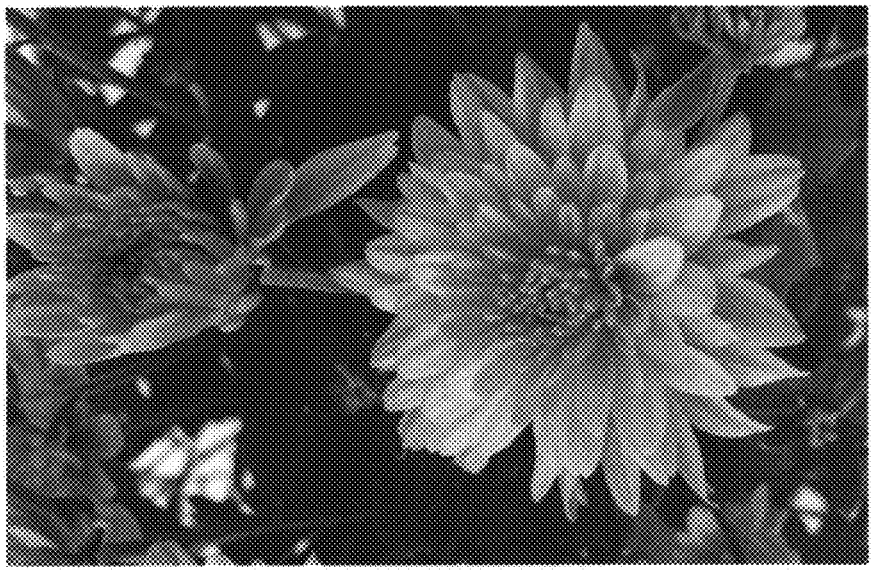

Latin name of the genus and species of the plant claimed: *Chrysanthemum×morifolium.*

Varietal denomination: 'CIFZ0057'.

BACKGROUND OF THE NEW PLANT

The present invention comprises a new *Chrysanthemum*, botanically known as *Chrysanthemum×morifolium*, and hereinafter referred to by the variety name 'CIFZ0057'.

'CIFZ0057' is a product of a planned breeding program. The new cultivar has medium sized (1.75+ inch) orange decorative flowers, compact sized plant with round mound habit and a natural season response in early September.

'CIFZ0057' originated from a cross made in February 2008 in Tenjo, Columbia. The female parent was the unnamed red colored seedling '05-M242'.

Compared to the female parent, 'CIFZ0057' has:

1. Similar inflorescence type that is larger in size with orange inflorescence color compared to the female parent that has a red color. Also ray floret tips are smooth not forked like the female parent.
2. Natural season response is similar but blackcloth response is half a week slower than the female parent.
3. Similar plant height but less plant width than the female parent.

The male parent was the unnamed pink/lavender seedling '04-M173'.

Compared to the male parent, 'CIFZ0057' has:

1. Larger inflorescence size with no disc florets and orange not pink/lavender inflorescence color like the male parent.
2. Natural season response is similar but blackcloth response is half a week slower than the male parent.
3. Similar plant height but less plant width than the male parent.

The resultant seed was sown in June 2013 in Gilroy, Calif.

The first act of asexual reproduction of 'CIFZ0057' was accomplished when vegetative cuttings were propagated from the initial selection, this initial selection took place in Oct. 11, 2013 in Monroeville, N.J.

BRIEF SUMMARY OF INVENTION

Horticultural examination of plants grown from cuttings of the plant initiated January 2014 in Mebane, N.C., and continuing thereafter, has demonstrated that the combination of characteristics as herein disclosed for 'CIFZ0057' are firmly fixed and are retained through successive generations of asexual reproduction.

'CIFZ0057' has not been observed under all possible environmental conditions. The phenotype may vary significantly with variations in environment such as temperature, light intensity and day length.

'CIFZ0057' has not been made publicly available prior to the effective filing date of this application, notwithstanding any disclosure that may have been made less than one year prior to the effective filing date of this application by the inventor or another who obtained 'CIFZ0057' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical inflorescence and foliage characteristics of 'CIFZ0057' with colors being as true as possible with an illustration of this type. The photographic drawings show in FIG. 1 a close view of inflorescences of the new variety and in FIG. 2 a flowering plant from an indoor trial.

Figure 2:
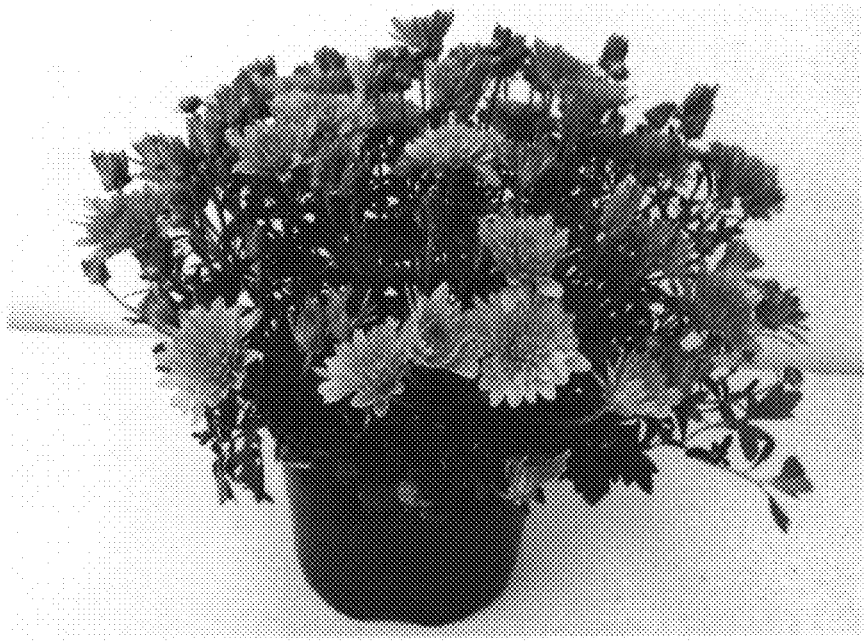

The aforementioned photographs: FIG. 1, as well as FIG. 2, were taken in August 2016 both showing a plant from the same blackcloth indoor trial in Gilroy, Calif. These plants were about 9 weeks of age. One rooted cutting per pot had been planted in a 6 inch pot in week 24, not pinched.

Shortday blackcloth treatment was applied from week 25 on. Plants started flowering in August.

DETAILED BOTANICAL DESCRIPTION

The measurements were taken in Gilroy, Calif. in August 2016 on the plants from the aforementioned trial.

Color references are made to The Royal Horticultural Society Colour Chart (R.H.S.) 2001.

TABLE 1

DIFFERENCES BETWEEN THE NEW VARIETY 'CIFZ0057' AND TWO MOST SIMILAR VARIETIES:

| | 'CIFZ0057' | 'Electra Amber Imp.' |
|---|---|---|
| Flowering response (blackcloth): | 0.5 week slower | 0.5 week faster |
| Inflorescence color: | Darker color | Lighter color |
| Inflorescence shape: | Flatter ray floret | More curved ray floret |
| Plant habit or size: | Smaller plant size | Bigger plant size |
| Inflorescence size: | Similar inflorescence size | Similar inflorescence size |

| | 'CIFZ0057' | 'Daybreak Dark Bronze' (No US Patent) |
|---|---|---|
| Flowering response (blackcloth): | Two days slower | Two days faster |
| Flowering response (natural): | Similar expect in the south where it can be a week slower than 'Daybreak Dark Bronze' | Similar except in the south where it can be a week faster than 'CIFZ0057' |
| Inflorescence color: | Similar | Similar |
| Inflorescence size: | Bigger inflorescence | Smaller inflorescence |
| Plant habit or size: | Similar | Similar |

Plant:

*Form, growth and habit.*—Herbaceous garden-type, stems upright and outwardly spreading, freely branching, strong and moderately vigorous growth habit.

*Plant height (above soil).*—11-13 cm.

*Plant height (inflorescence included).*—16-18 cm.

*Plant width.*—32-34 cm.

Roots:

*Number of days to initiate roots.*—About 4 days at about 22 degrees C.

*Number of days to produce a rooted cutting.*—14-16 days at 22 degrees C.

*Type.*—Fine, fibrous, free branching.

*Color.*—RHS N155B but whiter.

Foliage:

*Arrangement.*—Alternate.

*Immature leaf, color upper surface.*—RHS 141A.

*Immature leaf, color lower surface.*—RHS 137C.

*Mature leaf, color, upper surface.*—RHS 137A.

*Mature leaf, color lower surface.*—RHS 138A.

*Length.*—3.7-5.2 cm.

*Width.*—2.5-3.3 cm.

*Shape.*—Ovate.

*Base shape.*—Attenuate.

*Apex shape.*—Rounded to obtuse.

*Margin.*—3 main lobes, irregularly serrulated.

*Texture, upper surface.*—Bifid hairs.

*Texture, lower surface.*—Bifid hairs.

*Color of veins, upper surface.*—RHS 141C.

*Color of veins, lower surface.*—RHS 138A.

*Pattern of veining.*—Palmate.

*Petiole color.*—RHS 138A.

*Petiole length.*—1.3-1.8 cm.

*Diameter.*—0.2-0.25 cm.

*Texture.*—Covered with bifid hairs.

Stem:

*Quantity of main branches per plant.*—8-10.

*Color of stem.*—RHS 138B.

*Length of stem.*—8-10 cm.

*Diameter.*—0.3-0.5 cm.

*Length of internodes.*—0.5-0.75 cm.

*Texture.*—Bifid hairs.

*Color of peduncle.*—RHS 138A.

*Length of peduncle.*—5.3-6.0 cm.

*Peduncle diameter.*—0.15-0.2 cm.

*Texture.*—Bifid hairs.

Inflorescence:

*Type.*—Compositae, solitary, decorative-type inflorescences borne terminally above foliage, ray florets arranged on a capitulum.

*Quantity of short days to flowering (response time).*—About 5 weeks.

*Natural season flowering.*—Early September.

*Quantity of inflorescences per plant.*—40-75.

*Lastingness of individual blooms on the plant.*—About 5.5 weeks from first color.

*Fragrance.*—Slightly spicy.

Bud (when showing color):

*Color.*—RHS 13B, some shade of RHS 172C.

*Length.*—0.9-1.1 cm.

*Width.*—1.4-1.6 cm.

*Shape.*—Oblate.

Immature inflorescence:

*Diameter.*—3.0-3.3 cm.

*Color of ray florets, upper surface.*—RHS 13B, some shade of RHS 172B.

*Color of ray florets, lower surface.*—RHS 13C, shade of RHS 170C.

Mature inflorescence:

*Diameter.*—4.2-4.5 cm.

*Depth.*—1.2-1.5 cm.

*Total diameter of disc.*—No disc observed.

*Receptacle color.*—RHS 145A.

*Receptacle height.*—0.5 cm.

*Receptacle diameter.*—0.5 cm.

Ray florets:

*Average quantity of florets.*—Between 200 and 230 in many whorls.

*Color of florets, upper surface (abaxial).*—RHS 13C, shade of RHS 170B.

*Color inner surface (adaxial).*—RHS 12C, shade of RHS 170B.

*Length.*—1.4-1.6 cm.

*Width/diameter.*—0.35-0.5 cm.

*Shape.*—Oblong to elliptical.

*Apex shape.*—Most often emarginate or praemorse.

*Base shape.*—Attenuate.

*Margin.*—Entire.

*Texture, upper surface.*—Smooth, entire.

*Lower surface.*—Smooth, entire.

Disc florets: None present.

Phyllaries:

*Quantity.*—Approximately 25.

*Color, upper surface.*—RHS 139A.

*Color, lower surface.*—RHS 139B.

*Length.*—0.8-1.0 cm.

*Width.*—0.15-0.3 cm.

*Shape*.—Lanceolate.
*Apex shape*.—Acute.
*Base*.—Fused.
*Margins*.—Entire, some with papery edges.
*Texture, upper surface*.—Glabrous.
*Texture, lower surface*.—Bifid hairs.

Reproductive organs:
*Pistil*.—One.
*Length*.—0.3-0.5 cm.
*Style color*.—RHS 1C.
*Style length*.—0.35-0.4 cm.
*Stigma color*.—RHS 7D.
*Stigma shape*.—Bi-parted.
*Ovary color*.—RHS 145C.
*Ovary length*.—0.15 cm.
*Ovary width*.—0.1 cm.

Androecium:
*Stamens*.—None, as they are usually present in disc florets only, which are not developed.
*Fertility/seed set*.—Has not been determined to date.
*Disease/pest resistance*.—Has not been determined to date.

What is claimed is:

1. A new and distinct variety of *Chrysanthemum* plant named 'CIFZ0057' substantially as illustrated and described herein.

* * * * *